United States Patent [19]

Maeda et al.

[11] Patent Number: 5,464,857
[45] Date of Patent: Nov. 7, 1995

[54] 2-PHENYL-4,4,5,5-TETRAMETHYL-IMIDAZOLINE-1-OXYL-3-OXIDE DERIVATIVES AND THEIR USE AS THERAPEUTIC AGENTS FOR MAINTAINING BLOOD PRESSURE

[75] Inventors: Hiroshi Maeda, Kumamoto; Yoichi Miyamoto, Ibaraki; Takaaki Akaike, Kumamoto, all of Japan

[73] Assignee: Hiroshi Maeda, Kumamoto, Japan

[21] Appl. No.: 302,872

[22] PCT Filed: Nov. 21, 1994

[86] PCT No.: PCT No.: PCT/JP93/00044

§ 371 Date: Nov. 21, 1994

§ 102(e) Date: Nov. 21, 1994

[87] PCT Pub. No.: PCT Pub. No.: WO94/15921

PCT Pub. Date: Jul. 21, 1994

[51] Int. Cl.$^6$ ............... A61K 31/415; C07D 233/06
[52] U.S. Cl. ............... 514/398; 514/401; 548/354.1
[58] Field of Search ............... 548/354.1; 514/398, 514/401

[56] References Cited

U.S. PATENT DOCUMENTS

| 3,697,535 | 10/1972 | Leute et al. | 548/354.1 X |
| 3,758,495 | 9/1973 | Virkhaus | 548/354.1 X |
| 3,765,895 | 10/1973 | Fox | 96/088 |

OTHER PUBLICATIONS

Caneschi et al., Inorg. Chem., vol. 30, pp. 3936–3941 (1991).
Osiecki et al, J. Amer. Chem. Soc., vol. 90, No. 4, pp. 1078–1079 (1968).
Shemomura et al., J. Chem. Soc. Perkins Trans, II, pp. 795–798 (1988).

Primary Examiner—Floyd D. Higel
Attorney, Agent, or Firm—Wenderoth, Lind & Ponack

[57] ABSTRACT

(1) The imidazoline derivative represented by the following general formula (1)

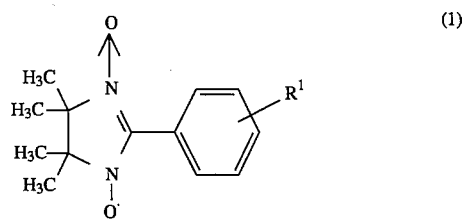

where $R^1$ is a substituent endowed with water solubility or fat solubility, particularly carboxyl group or carboxymethoxy group or a pharmaceutically acceptable salt thereof, (2) The method for producing the above-mentioned compound, and (3) A therapeutic agent containing as its active ingredient the above-mentioned imidazoline derivative or an imidazoline derivative wherein $R^1$ indicated in the formula (1) is hydrogen atom. The imidazoline derivative set forth under (1) above is a novel substance; and this compound itself and its derivative having $R^1$ as indicated in the general formula (1) is hydrogen atom are useful as a therapeutic agent for treatment of shock from the fall in blood pressure by virtue of their ability to remove excess NO which is the vascular endothelium-derived relaxing factor (EDRF).

11 Claims, No Drawings

2-PHENYL-4,4,5,5-TETRAMETHYL-IMIDAZOLINE-1-OXYL-3-OXIDE DERIVATIVES AND THEIR USE AS THERAPEUTIC AGENTS FOR MAINTAINING BLOOD PRESSURE

FIELD OF THE INVENTION

The present invention relates to novel 2-phenyl-4,4,5,5-tetramethylimidazoline-1-oxyl-3-oxide derivatives, their use as highly safe therapeutic agents for maintaining blood pressure having an imidazoline derivative as the active ingredient and intended for maintaining blood pressure of man for treatment of shock by means of removing excess nitric oxide (hereinafter referred to as "NO") which is the very substance constituting endothelium-derived relaxing factor (hereinafter referred to as "EDRF"), which causes relaxation of the vascular smooth muscles.

DESCRIPTION OF THE PRIOR ART

In the past it was well known that the vascular endothelial cells secrete a substance contributing to relaxation of the vascular smooth muscles, i.e. EDRF. (Ref. Nature, Vol. 288, 373–376, 1980). After a while it was substantiated that NO produced from L-arginine is the very substance which constitutes EDRF. (Ref. Nature, Vol. 327, 524–526, 1987; and Proc. Natl. Acad. Sco., USA, Vol. 84, 9265–9269, 1987).

There exist as NO-synthesizing enzymes (NO synthase) produced by the endothelial cells the following two kinds of enzymes: (1) the endogenous type which is always present in the vascular endothelium (Ref. Pharm. Rev., Vol. 43, 109–142, 1991; The Lancet, Vol. ii, 997–1000, 1989) and (2) the type which is derived from endotoxin or cytokines such as tumor necrosis factor (TNF)(Ref. Pharm. Rev., Vol. 43, 109–142, 1991). While the former type (1) is thought to contribute to physiological adjustment of the vascular resistance, the abrupt progress of the synthesis of NO due to the latter type (2) is considered to cause the decline in the vascular resistance and the accompanying fall in blood pressure, presumably causing shock. Most of the patients having syndrome do not respond to a vasopressor such as norepinephrine and dopamine and fail to recover.

Various therapies have been studied to cope with such shock as described above caused by endotoxin or cytokines. One of those therapeutic approaches was intended to treat laboratory animals in endotoxin shock or patients in septic shock, using L-arginine analogue which is an NO synthase inhibitor. (Ref. The Lancet, Vol. 338, 1555–1557, 1991, and the Lancet, Vol. 338, 1557–1558, 1991). Since the increasing production of EDRF (namely, NO) is the conclusive and universal phenomenon which occurs with the fall in blood pressure of the patient in endotoxin shock, the effort to decrease the amount of NO is an excellent therapeutic approach to treat endotoxin shock or similar cases. Such a therapeutic agent capable of neutralizing the action of NO by itself is to advantageous in consideration of the complexity involved in the therapy to neutralize the action of endotoxin or individual cytokine.

Nevertheless, there have been presented reports to the effect that caution must be taken in determining the dosage to be administered, since the effect of this NO synthase inhibitor to maintain blood pressure when administered for treatment of shock strongly depends on the dosage such that if it is too little, its efficacy is totally lost, and, conversely, if the dosage is excessive, the patient is led to an extremely dangerous condition as is induced by violent rise and fall in the blood pressure (Ref. The Lancet, Vol. 338, 1555–1557, 1991; The Lancet, Vol. 338, 1557–1558, 1991. In view of the significance of the aforementioned reports, there still remain unresolved problems associated with safety of the NO synthase inhibitor. Moreover, since the NO synthase inhibitor is an L-arginine derivative, there is a possibility that this inhibitor adversely affects L-arginine-dependent protein synthesizing systems other than the NO synthase as well as metabolic systems such as the (Krebs-Henseleit) urea cycle. In this sense, use of such inhibitor is feared that the administration of this NO synthase inhibitor can be accompanied by some side effects. In particular, it will conceivably give rise to many unknown questions if the inhibitor is administered in a copious amount over an extensive period of time.

The present inventors have studied a method for stably maintaining blood pressure by removing excess NO produced, for the purpose of resolving the aforementioned problem, without administering any NO synthase inhibitor.

Meanwhile, although there have been reported a method for producing cigarette filter impregnated with 2-phenyl-4,4,5,5-tetramethylimidazoline-1-oxyl-3-oxide (hereinafter referred to as "PTIO"), which is represented by the general formula cited hereinafter with $R^2$ indicated therein being hydrogen atom, for the purpose of removing NO from cigarette smoke (Ref. B. P. 1235880), and another method which employs PTIO as the NO oxidizing agent in the instrument to determine nitrogen oxides (NO and $NO_2$) in atmosphere (Ref. "Kankyo To Sokutei Gijutsu" (Environment and Measuring Technology), Vol. 12, 32–39, 1985) it is not known that compounds represented by the general formula (2), including PTIO, are effective to maintain blood pressure.

SUMMARY OF THE INVENTION

The present inventors, as the result of their study on the efficacy of PTIO and its derivatives as a therapeutic agent to maintain blood pressure, have discovered those various novel PTIO derivatives represented by the following general formula (1) with the phenyl group of PTIO being substituted by a specific substituent and the method for producing the same, and also that the PTIO represented by the general formula (2), and a component containing the above-mentioned novel PTIO derivative, impart the effectiveness peculiar to a therapeutic agent to maintain blood pressure, and thus have finally completed the present invention.

The object of the present invention is, therefore, to provide an effective and safe therapeutic agent to maintain blood pressure with a novel compound having the efficacy as a therapeutic agent to maintain blood pressure possessing a new mechanism of action of eliminating NO.

That is to say, the present invention comprises a therapeutic agent to maintain blood pressure which contains as its active ingredients the imidazoline derivative represented by the general formula (1)

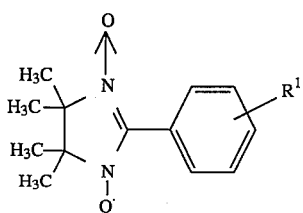

where $R^1$ is a substituent endowed with water solubility or fat solubility, or a pharmaceutically acceptable salt thereof, and the imidazoline derivative represented by the following general formula (2)

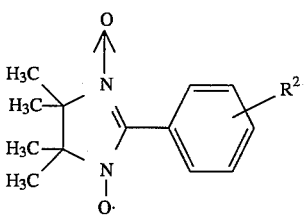

where $R^2$ is a substituent given hydrogen atom, a substituent endowed with water solubility or fat solubility, or a pharmaceutically acceptable salt thereof.

Preferably selected for $R^1$ indicated in the general formula (1), which being a substituent endowed with water solubility or fat solubility or a pharmaceutically acceptable salt thereof, is carboxyl group or carboxymethoxy group or a pharmaceutically acceptable salt thereof.

Preferably selected for the imidazoline derivative utilized as the therapeutic agent to maintain blood pressure of the present invention, which is represented by the general formula (2), is such an imidazoline derivative with $R^2$ as indicated in the formula being hydrogen atom, carboxyl group or carboxymethoxy group or a pharmaceutically acceptable salt thereof.

As the pharmaceutically acceptable salt, sodium salt or potassium salt is particularly preferable.

As for the synthesis of PTIO represented by the general formula (2) with $R^2$ as indicated therein being hydrogen atom, it is well known that it is obtained by reacting 2,3-bis-(hydroxyamino)-2,3-dialkylbutane with benzaldehyde. (Ref. J. Am. Chem. Soc., Vol. 90, 078–1079, 1968).

On the other hand, the novel imidazoline derivative represented by the general formula (1) can be produced by reacting 2,3-bis-(hydroxyamino)-2,3-dialkylbutane with a benzaldehyde derivative. For example, 2-(4-carboxyphenyl)-4,4,5,5-tetramethylimidazoline-1-oxyl-3-oxide (hereinafter referred to as "C-PTIO") represented by the general formula (1) with $R^1$ as indicated therein being carboxyl group or a pharmaceutically acceptable salt thereof can be obtained by causing 2,3-bis-(hydroxyamino)-2,3-dialkylbutane to react with p-formylphenoxybenzoic acid.

Additionally, 2-(4-carboxymethoxylphenyl)-4,4,5,5-tetramethylimidazoline-1-oxyl-3-oxide (hereinafter referred to as "CM-PTIO") represented by the general formula (1) with $R^1$ as indicated therein being carboxymethoxyl group or a pharmaceutically acceptable salt thereof can be obtained by causing 2,3-bis-(hydroxyamino)-2,3-dialkylbutane to react with p-formylphenoxyacetic acid.

The PTIO and the imidazoline derivative having the substituent indicated in the general formula (1) (hereinafter collectively referred to as "PTIO and its derivatives") which are thus produced can be identified by $^1$H-nuclear magnetic resonance (NMR), infrared absorption spectrometry, mass spectrometry or electron spin resonance (ESR) analysis of the obtained product and intermediates thereof.

The therapeutic agent to maintain blood pressure disclosed by the present invention may be utilized as a composition containing effective and low toxicity contents. The effective and low-toxicity dosage is 5–500 mg/kg-weight/day.

The therapeutic agent to maintain blood pressure disclosed by the present invention may be administered in the form of injection, oral dosage, suppository or aerosol spray.

In the case of injection, any of the subcutaneous, intramascular, intravenous, and intra-arterial routes is workable. It is also possible to infuse it by continuous intravenous infusion. In the case of injection, although there is not imposed any limitation on the concentrations of PTIO and its derivative, it is preferable that the concentrations of PTIO and its derivative be 0.001–5% by weight. It is also possible that PTIO and its derivative, both being prepared in powder form, are combined with a liquid solvent to be administered as an injection.

The type of preparation for oral administration may be selected optionally. Some examples of this type are tablet, granules, pill, liquid medicine, syrup, troche, and drops. All of these preparations may be manufactured conventionally. Furthermore, PTIO and its derivative may be suspended in oil so that enteral absorption may be enhanced.

PTIO and its derivative can be formed by a conventional method into a suppository for anal or vaginal application.

Aerosol spray preparation may be manufactured conventionally, using a suitable propellant.

PTIO and its derivative react with NO at the molar ratio of 1 to 1, and are converted, with one oxygen atom added thereto, into nitrogen dioxide (hereinafter referred to as "$NO_2$") which is inactive to vascular smooth muscular cells. $NO_2$ is, furthermore, converted into nitrous ion and nitrate ion in aqueous solution. The present inventors have discovered that PTIO and its derivative themselves are converted into substances inactive to NO, that PTIO and its derivative forcefully suppress relaxation of the NO-dependent vascular smooth muscles, and also that the blood pressure and the pulse rate of animals given PTIO and its derivative stably remained at normal levels even if NO-saturated aqueous solution was infused into their blood vessels. As has been discussed, PTIO and its derivative do not obstruct the synthesis of NO, but eliminates excess NO produced. Hence, they do serve as a highly safe therapeutic agent to maintain blood pressure.

DESCRIPTION OF THE PREFERRED EMBODIMENT(S)

The present invention shall be explained in detail with the following examples:

EXAMPLE 1

Synthesis of 2-(4-carboxyphenyl)-4,4,5,5-tetramethyl-imidazoline-1-oxyl-3-oxide (C-PTIO)

24.6 g of 2,3-bis-(hydroxyamino)-2,3-dimethylbutane sulfate was dissolved in 100 ml of water. After neutralized with 1M $KHCO_3$ with cooling on ice, the solution was added with 15.0 g of p-formylbenzoic acid and was agitated overnight at room temperature. The precipitate was dried and 16.9 g of 1,3-dihydroxy-4,4,5,5-tetramethyl 2-(4-carboxyphenyl)imidazole (I) was obtained.

After the said intermediate (I) was subjected to observation by $^1$H-NMR, and fast atomic bombardment mass spectrometry (FAB-MS) for identification, the sample was verified to be the above-mentioned intermediate (I) with the following test results:

(1) $^1$H-NMR (DMSO -$d_6$) δ: 7.73 (dd, 4H, Ar—H) 4.57 (s, 1H, C—H) 4.10 (broad s, 2H, NOH) 1.05 (s, 6H, $CH_3$) 1.09 (s, 6H, $CH_3$)

(2) FAB-MS m/z 279 (M-H)$^{31}$

Next, 14.0 g of (I) was dissolved in 100 ml of N,N-dimethylformaldehyde, and the solution was added with 23.5 g of $PbO_2$ to succeedingly undergo reaction for 3 hours at room temperature. Then, $PbO_2$ was filtered out. After the concentrated residue of the filtrate was dissolved in water, the solution was freeze-dried and thus was obtained 12.5 g of C-PTIO. By infrared absorption spectrometry, mass spectrometry, 1H-nuclear NMR and ESR, the product thus obtained was identified to be as follows:

(1) IR (KBr disk): 1360 cm$^{-1}$ (N—O )

(2) FAB-MS m/z 276 (M-H)$^-$ (3) 1H - NMR ($D_2O$) δ: 2.90 (d, 12H, $CH_3$) 7.90 (s, 4H, Ar—H)

(4) ESR (0.25M phosphoric acid buffer, pH7.5) $a_N^{1.3}$= 0.81 mT

On the basis of the above-mentioned test results, it was verified that the product is 2-(4-carboxy-phenyl)-4,4,5,5-tetramethyl-imidazoline-1-oxyl 3-oxide (C-PTIO).

EXAMPLE 2

Synthesis of 2-(4-carboxy-methoxyphenyl)-4,4,5,5-tetramethyl-imidazoline-1-oxyl-3-oxide (CM-PTIO)

24.6 g of 2,3-bis-(hydroxyamino)-2,3-dimethylbutane sulfate was dissolved in 100 ml of water. After the solution was neutralized with 1M $KHCO_3$ with cooling in ice, it was added with 18.0 g of p-phenoxyacetic acid, and was agitated overnight at room temperature. Then, the produced precipitate was dried, and was dissolved in 100 ml of N,N-dimethylformaldehyde. After 45 g of $PbO_2$ was added, the liquid underwent reaction for 3 hours at room temperature. After filtering out $PbO_2$, the filtrate was concentrated. The residue was dissolved in water, and this aqueous solution was freeze-dried to obtain 15.1 g of CM-PTIO. The analytical value thus determined are as follows:

(1) IR (KBr disk): 1360 cm$^{-1}$ (N—O)

(2) FAB-MS m/z 306 (M-H)$^-$ (3) 1H-NMR($D_2O$) δ: 1.35 (d, 12H, $CH_3$) 1.65 (s, 2H, $CH_2$) 7.10 (d, 2H, Ar—H) 8.05 (d, 2H, Ar—H)

(4) ESR (0.25M phosphoric acid buffer, pH 7.5) $a_N^{1.3}$= 0.82 mT

On the basis of these test results, the product was identified to be 2-(4-carboxymethoxyphenyl)-4,4,5,5-tetramethylimidazoline-1-oxyl-3-oxide (CM-PTIO).

EXAMPLE 3

Production of C-PTIO injection

C-PTIO was dissolved in 800 ml of distilled water for injection use. After adding sodium chloride to this aqueous solution, an injection preparation of 100 ml total volume was obtained by adding distilled water for injection as needed. After sterilizing the solution by letting it pass through bacterial filter, a C-PTIO injection preparation having the following ingredients was obtained:

| | |
|---|---|
| C-PTIO | 2.0 g |
| Sodium chloride | 9.0 g |
| Distilled water for injection | Appropriate volume |
| Total volume | 1,000 ml |

EXAMPLE 4

Production of PTIO preparation

PTIO, lactose and starch were mixed and formed into wet granules with aqueous solution of polyvinylpyrrolidone. After the obtained material was dried and sifted, the granules were kneaded with magnesium stearate and compressed into tablets, each of which weighing 500 mg and consisting of the following ingredients:

| | |
|---|---|
| PTIO | 100 weight parts |
| Lactose | 235 weight parts |
| Starch | 50 weight parts |
| Polyvinylpyrrolidone | 50 weight parts |
| Magnesium stearate | 5 weight parts |

EXAMPLE 5

Production of CM-PTIO suppository

The following ingredients were melt-mixed and formed into 10 pieces of suppositories:

| | |
|---|---|
| CM-PTIO | 5.0 g |
| Macrogol 4000 (polyethyleneglycol) | 2.0 g |
| Macrogol 1500 (polyethyleneglycol) | 9.0 g |

EXAMPLE 6

Suppression of EDRF-dependent relaxation (dilation) of vascular smooth muscles by therapeutic agent to maintain blood pressure Rabbit aorta with vascular endothelium unremoved was cut into the ring-form and was hung in organ bath filled with Krebs-Ringer's solution and its tension was continuously recorded. After the rabbit aorta was contracted by exposure to 0.15 microM phenylephrine, it was completely dilated by adding 3 microM acetylcholine. It is well known that the dilation of the vascular smooth muscle by acetylcholine is dependent on EDRF, namely NO. The degree of PTIO's ability to suppress dilation caused by acetylcholine was determined by adding C-PTIO or CM-PTIO prepared in EXAMPLES 1–2 in such manners that the concentration would be registered at 30 microM, 100 microM and 300 microM, respectively. Used as a reference was $N^G$-methyl-arginine, which is NO synthase inhibitor, at the corresponding concentrations. The test result is shown in Table 1.

TABLE 1

The ability to suppress EDRF-dependent relaxation (dilation) of vascular smooth muscles of PTIO, C-PTIO, CM-PTIO and $N^G$-methyl-arginine Percentage of suppression against relaxation of vascular smooth muscles

| Concentration (microM) | PTIO | C-PTIO | CM-PTIO | $N^G$-methyl-arginine |
|---|---|---|---|---|
| 0 | 0 | 0 | 0 | 0 |
| 30 | 25.1 ± 2.0 | 47.2 ± 5.5 | 26.5 ± 1.9 | 21.3 ± 3.2 |
| 100 | 52.4 ± 4.6 | 72.5 ± 2.0 | 46.5 ± 1.8 | 48.7 ± 9.5 |
| 300 | 78.5 ± 1.3 | 93.0 ± 1.8 | 84.5 ± 6.6 | 74.5 ± 5.0 |

Note 1: The vascular smooth muscles which were contracted by 0.15 microM phenylephrine was relaxed (dilated) by 100% by 3.0 miroM acetylcholine. The percentage of suppression against relaxation was given the rating of 0%.

Note 2: Each measurement represents the mean average of 10 test results plus minus standard deviation. As can be obviously seen from Table 1, PTIO, C-PTIO, and CM-PTIO suppressed the EDRF-dependent relaxation of vascular smooth muscles, concentration-dependently. The intensity of suppression effected by PTIO and CM-PTIO was either equivalent to or somewhat more intensive than that of $N^G$-methyl-arginine. The intensity of suppression by C-PTIO was twice as stronger than the said substances.

EXAMPLE 7

The effect of PTIO's suppression against the decline in blood pressure caused by intravenous infusion of aqueous solution of NO Tail veins of rats anesthetized with Nembutal (pentobarbital sodium) were cannulated to establish the route for intravenous administration of therapeutic agent. The average blood pressure and the pulse rate were monitored on the basis of the pulse pressure wave of the tail artery, using an automatic blood pressure measuring apparatus (PS-200) manufactured by Riken Kaihatsu Company, Limited.

2.0 mg/ml of PTIO injection prepared according to the manufacturing example 1 was administered to the first group of rats by continuous intravenous infusion at the rate of 6.0 ml/hour for 10 minutes. After the lapse of 4 minutes from then, 1.0 ml of NO-saturated physiological solution of sodium chloride was continuously infused intravenously. For the second group of rats, PTIO was not administered, but NO was administered similarly instead. Except for the period in which the said dosage was administered, physiological solution of sodium chloride was administered by continuous intravenous infusion at the rate of 6.0 ml/hour. All the while, the blood pressure and the pulse rate were continuously monitored, and additionally the ratio of blood pressure and pulse rate recorded five minutes after the administration of the dosage to those recorded five minutes prior to the administration of the same was calculated. The test result is shown in Table 2.

TABLE 2

The effect of PTIO on changes in blood pressure and pulse rate caused by administration of NO

| Specimen Group | Blood pressure (% to prior to administration of NO) | Pulse rate (% to prior to administration of NO) |
|---|---|---|
| 1 | 93.1 ± 2.3 | 96.5 ± 6.4 |
| 2 | 55.8 ± 1.8 | 126.3 ± 2.0 |

LEGEND:
"Specimen Group 1": A group of 3 rats to which 2 mg/ml of PTIO was administered at the rate of 6 ml/hour for 10 minutes.
"Specimen Group 2": A reference group of 3 rats to which PTIO was not administered.
The measurement represents the average plus minus standard deviation.

According to Table 2, although the blood pressure dropped about 40% and the pulse rate increased about 20% in consequence of the administration of NO-saturated physiological solution of sodium chloride (Specimen Group 2), the changes in blood pressure and pulse rate were almost nil if PTIO had been administered beforehand. (Specimen Group 1)

POSSIBILITY OF INDUSTRIALLY CARRYING OUT THE INVENTION

The present invention is to provide a therapeutic agent to maintain blood pressure for treatment of shock. High safety is achievedd in therapeutic use of this agent intended to maintain blood pressure in the treatment of shock due to the fall in blood pressure caused by burns, septicemia, stings by bees, wasps and hornets, snakebite, anaphylaxis, poisoning caused by organophosphorous agents, or side effect of various cytokine therapies. It is also possible to use it as an efficacy accelerant for cardiac.

We claim:

1. The imidazoline derivatives represented by the following formula (1)

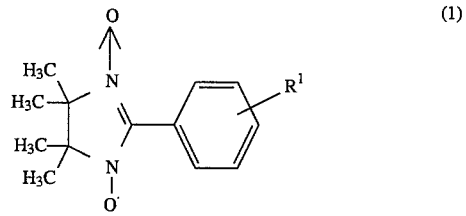

where $R^1$ is a water-solubilizing or fat-solubilizing substituent; or a pharmaceutically acceptable salt thereof.

2. The imidazoline derivatives according to claim 1, wherein $R^1$ is carboxyl group or a pharmaceutically acceptable salt thereof.

3. The imidazoline derivatives according to claim 1, wherein $R^1$ is carboxylmethoxy group or a pharmaceutically acceptable salt thereof.

4. A therapeutic agent for maintaining blood pressure containing as its active ingredient the imidazoline derivatives represented by the formula (2) below:

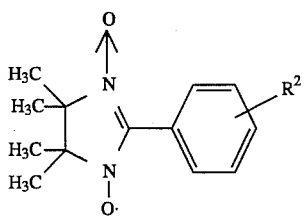

(2)

where $R^2$ is hydrogen atom, or water-solubilizing or fat-solubilizing substituent; or a pharmaceutically acceptable salt thereof.

5. A therapeutic agent for maintaining blood according to claim 4, containing as its active agent 2-phenyl-4,4,5,5-tetramethyl-imidazoline-1-oxyl-3-oxide or a pharmaceutically acceptable salt thereof.

6. The therapeutic agent for maintaining blood pressure according to claim 4, containing as its active agent the imidazoline derivatives of the formula

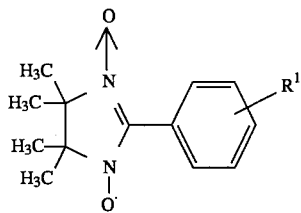

where $R^1$ is a carboxyl group or a pharmaceutically acceptable salt thereof.

7. The therapeutic agent for maintaining blood pressure according to claim 4, containing as its active agent the imidazoline derivatives of the formula

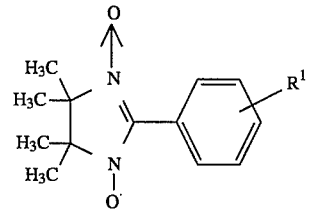

where $R^1$ is a carboxylmethoxy group or a pharmaceutically acceptable salt thereof.

8. The therapeutic agent for maintaining blood pressure according to claim 4, wherein the therapeutically acceptable salt is potassium or sodium salt.

9. The therapeutic agent for maintaining blood pressure according to claim 5, wherein the therapeutically acceptable salt is potassium or sodium salt.

10. The therapeutic agent for maintaining blood pressure according to claim 6, wherein the therapeutically acceptable salt is potassium or sodium salt.

11. The therapeutic agent for maintaining blood pressure according to claim 7, wherein the therapeutically acceptable salt is potassium or sodium salt.

\* \* \* \* \*